US010967206B2

(12) United States Patent
Cho

(10) Patent No.: US 10,967,206 B2
(45) Date of Patent: Apr. 6, 2021

(54) VALVE STRUCTURE FOR RESPIRATOR

(71) Applicant: Shih-Hsiung Cho, Taipei (TW)

(72) Inventor: Shih-Hsiung Cho, Taipei (TW)

(73) Assignee: MAKRITE INDUSTRIES INC., New Taipei (TW)

( * ) Notice: Subject to any disclaimer, the term of this patent is extended or adjusted under 35 U.S.C. 154(b) by 571 days.

(21) Appl. No.: 15/872,917

(22) Filed: Jan. 16, 2018

(65) Prior Publication Data

US 2019/0217133 A1 Jul. 18, 2019

(51) Int. Cl.
*A62B 9/02* (2006.01)
*A61M 16/20* (2006.01)
*A62B 18/10* (2006.01)
*F16K 15/14* (2006.01)
*F16K 15/00* (2006.01)
*F16K 27/02* (2006.01)
*A62B 7/10* (2006.01)
*A62B 23/02* (2006.01)

(52) U.S. Cl.
CPC ............. *A62B 9/02* (2013.01); *A61M 16/202* (2014.02); *A62B 18/10* (2013.01); *F16K 15/00* (2013.01); *F16K 15/148* (2013.01); *F16K 27/0209* (2013.01); *A62B 7/10* (2013.01); *A62B 23/025* (2013.01)

(58) Field of Classification Search
CPC ......... A62B 9/02; A62B 18/10; A62B 23/025; A61M 16/208
See application file for complete search history.

(56) References Cited

U.S. PATENT DOCUMENTS

| 4,965,955 | A | * | 10/1990 | Campbell | ............ | A01K 63/02 |
| | | | | | | 119/201 |
| 6,860,267 | B2 | * | 3/2005 | Capon | ................ | A62B 23/02 |
| | | | | | | 128/201.25 |
| 7,866,319 | B2 | * | 1/2011 | Penton | ................. | A62B 7/04 |
| | | | | | | 128/205.24 |
| 2005/0145249 | A1 | * | 7/2005 | Solyntjes | ............ | A62B 23/02 |
| | | | | | | 128/205.25 |
| 2015/0151143 | A1 | * | 6/2015 | Langford | ............ | A62B 18/02 |
| | | | | | | 128/205.24 |

FOREIGN PATENT DOCUMENTS

WO WO-2016167532 A1 * 10/2016 ............. A62B 18/10

* cited by examiner

*Primary Examiner* — Jan Christopher L Merene
*Assistant Examiner* — Matthew Standard
(74) *Attorney, Agent, or Firm* — Che-Yang Chen; Law Office of Michael Chen

(57) ABSTRACT

A valve structure for a respirator includes a base, an upper cover, a membrane and a discharge device, wherein an outer side of an upper annular wall of the upper cover is provided with multiple L-shaped engagement blocks, and a combination hole of the discharge device is provided with multiple L-shaped engagement blocks embedded with the L-shaped engagement blocks of the upper annular wall, so that the discharge device is combined with the upper cover.

5 Claims, 14 Drawing Sheets

VALVE STRUCTURE FOR RESPIRATOR

BACKGROUND OF THE INVENTION

(1) Field of the Invention

The invention relates to a valve structure for a respirator, and more particularly to a valve structure used in a respirator.

(2) Description of the Prior Art

A respirator is one of today's indispensable hygiene products, and is mainly worn on the user's mouth and nose portions. The respirator blocks the dirty, dust or germ from the outside air when the user is breathing. In order to increase the efficiency of the respirator, many manufacturers have made many improvements on the respirator or added some accessories to the respirator. As shown in FIG. 1, a valve 11 is mainly disposed on the surface of a respirator 1. When the user inhales, the external dirty, dust or germ is filtered mainly through the body of the respirator 1. When the user exhales, the exhaled gas is rapidly discharged from the respirator 1 through holes 110 on the valve 11. Thus, the exhaled gas is rapidly discharged to enhance the wearer's comfort. Although the valve 11 can discharge the exhaled gas, the passive discharge method cannot timely and rapidly discharge the gas, and valve 11 cannot be assembled with other additional assistant devices or components, and is still slightly inconvenient in use.

Therefore, how to improve the above-mentioned drawbacks and problems is the technical difficulty that the inventor wants to solve.

SUMMARY OF THE INVENTION

A main objective of the invention is to provide a valve structure for a respirator. The valve structure is mainly composed of a base, an upper cover, a membrane and a discharge device. The upper annular wall of the upper cover has multiple L-shaped engagement blocks on the outer side. And the combination hole of the discharge device also has multiple L-shaped engagement blocks, which are embedded into the L-shaped engagement blocks of the upper annular wall, so that the discharge device is assembled with the upper cover.

Further aspects, objects, and desirable features of the invention can be better understood using the following detailed description and drawings, which various embodiments of the disclosed invention are illustrated by examples.

DETAILED DESCRIPTION OF THE PREFERRED EMBODIMENTS

Figure 1:
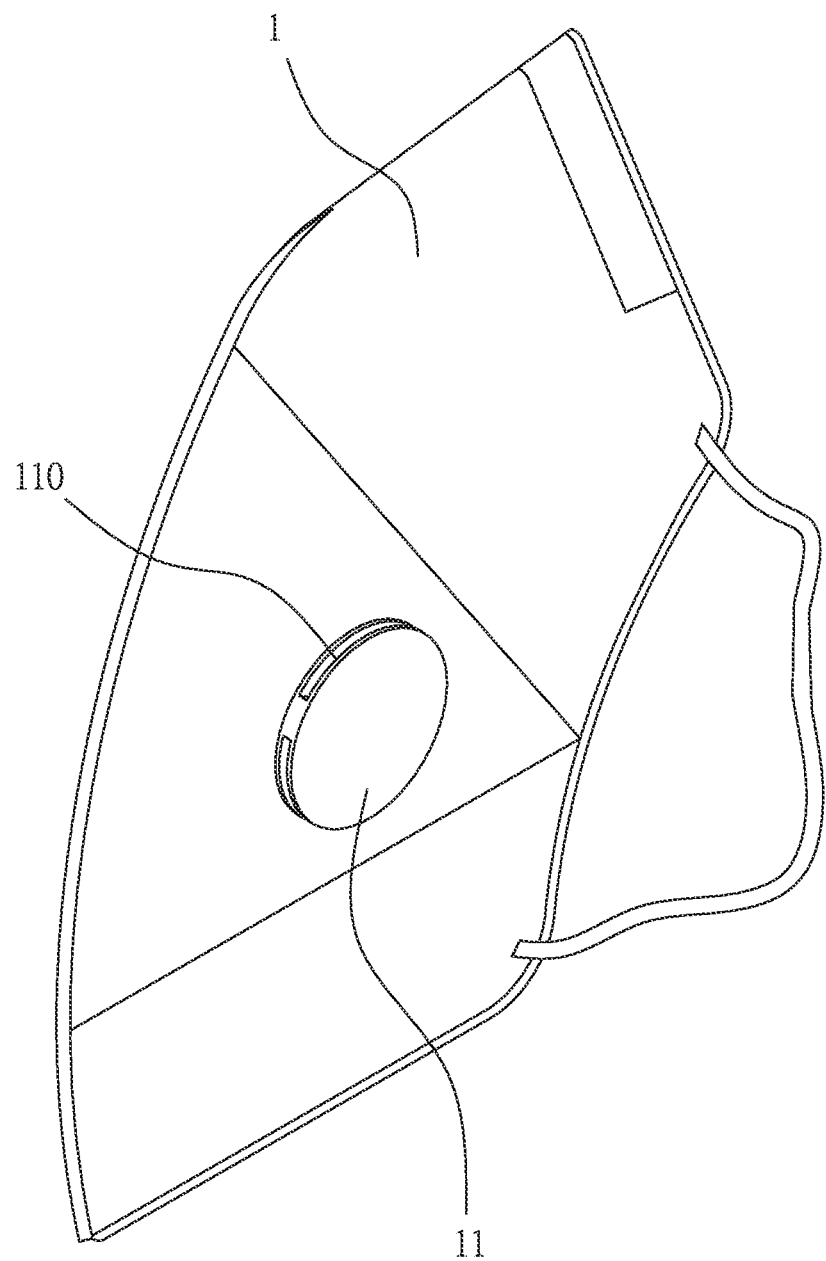
FIG. 1 shows an exterior illustration of the prior art.
Figure 2:
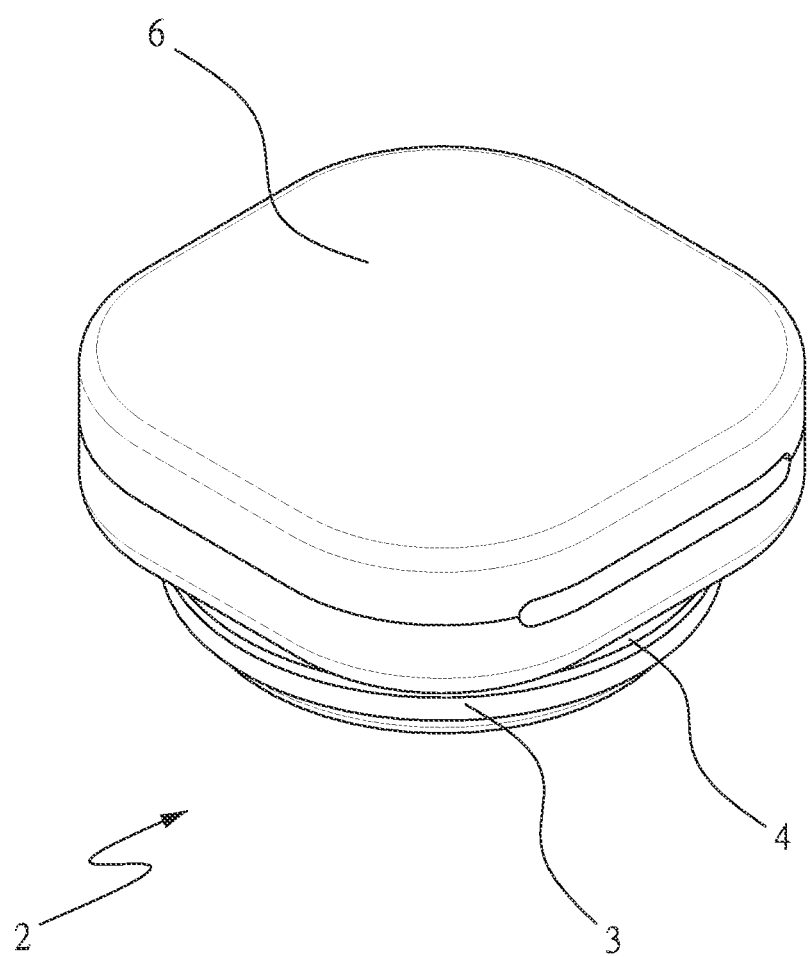
FIG. 2 shows an exterior illustration of the invention.
Figure 3:
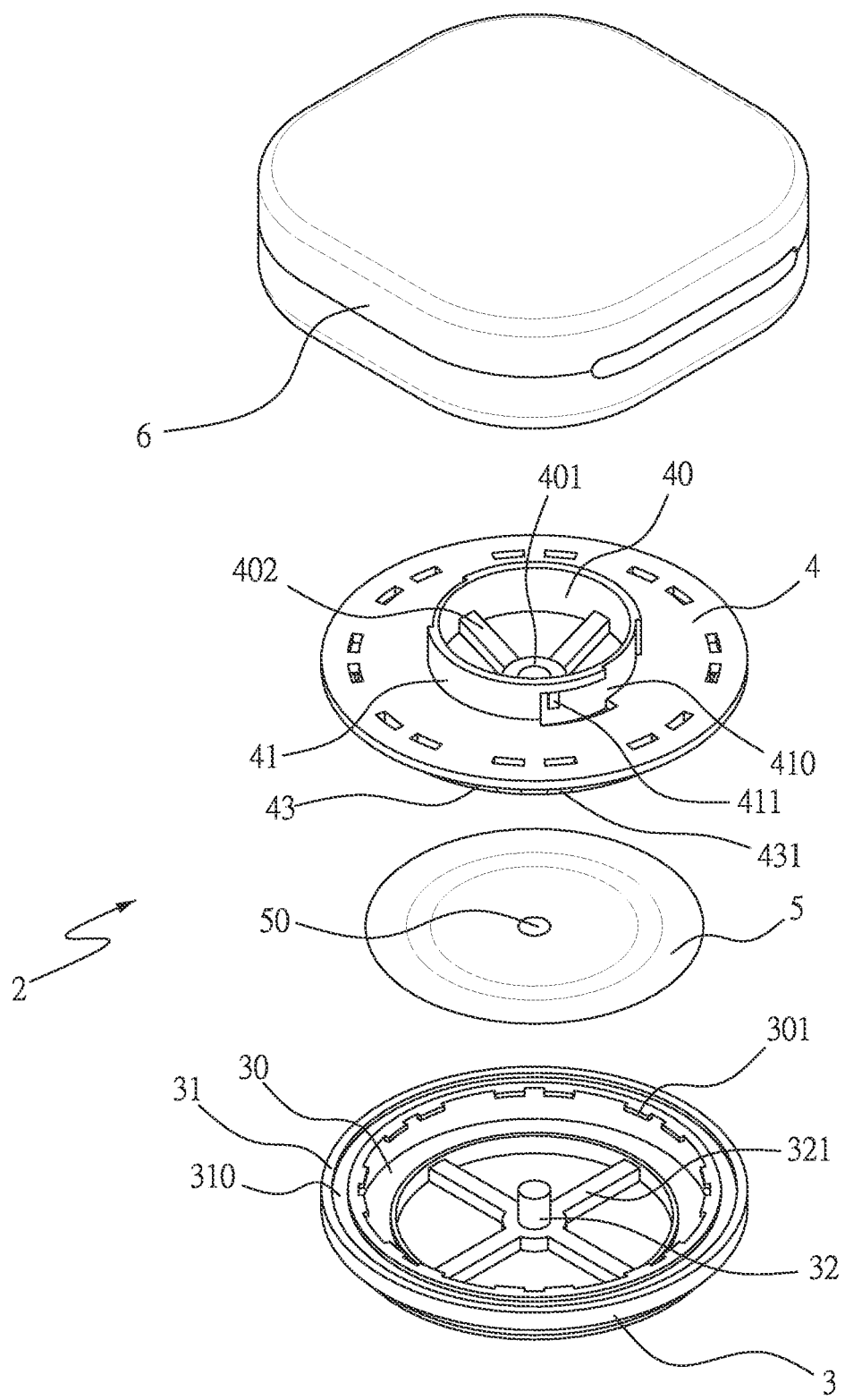
FIG. 3 shows a first exploded view of the invention.
Figure 4:
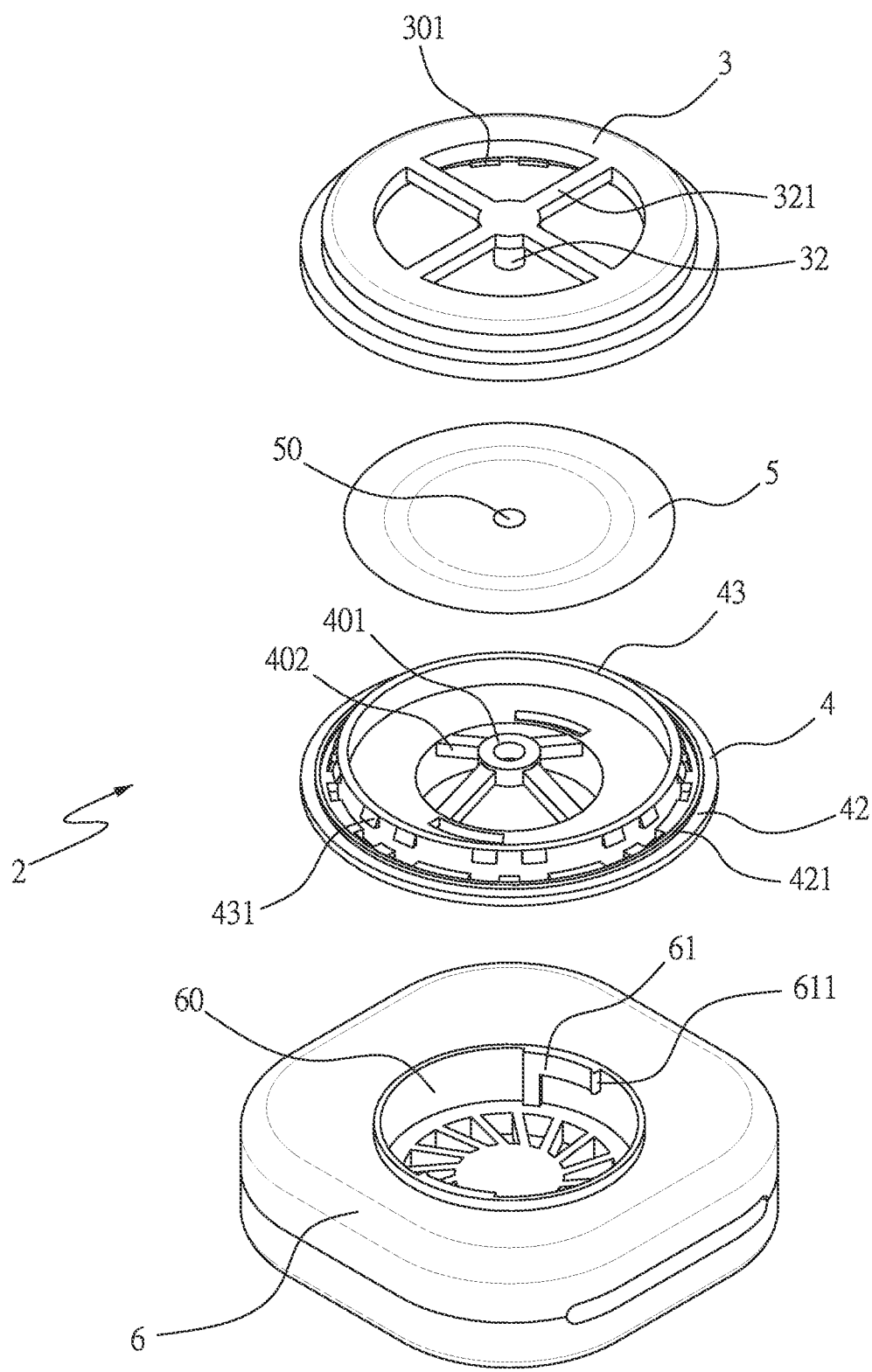
FIG. 4 shows a second exploded view of the invention.
Figure 5:
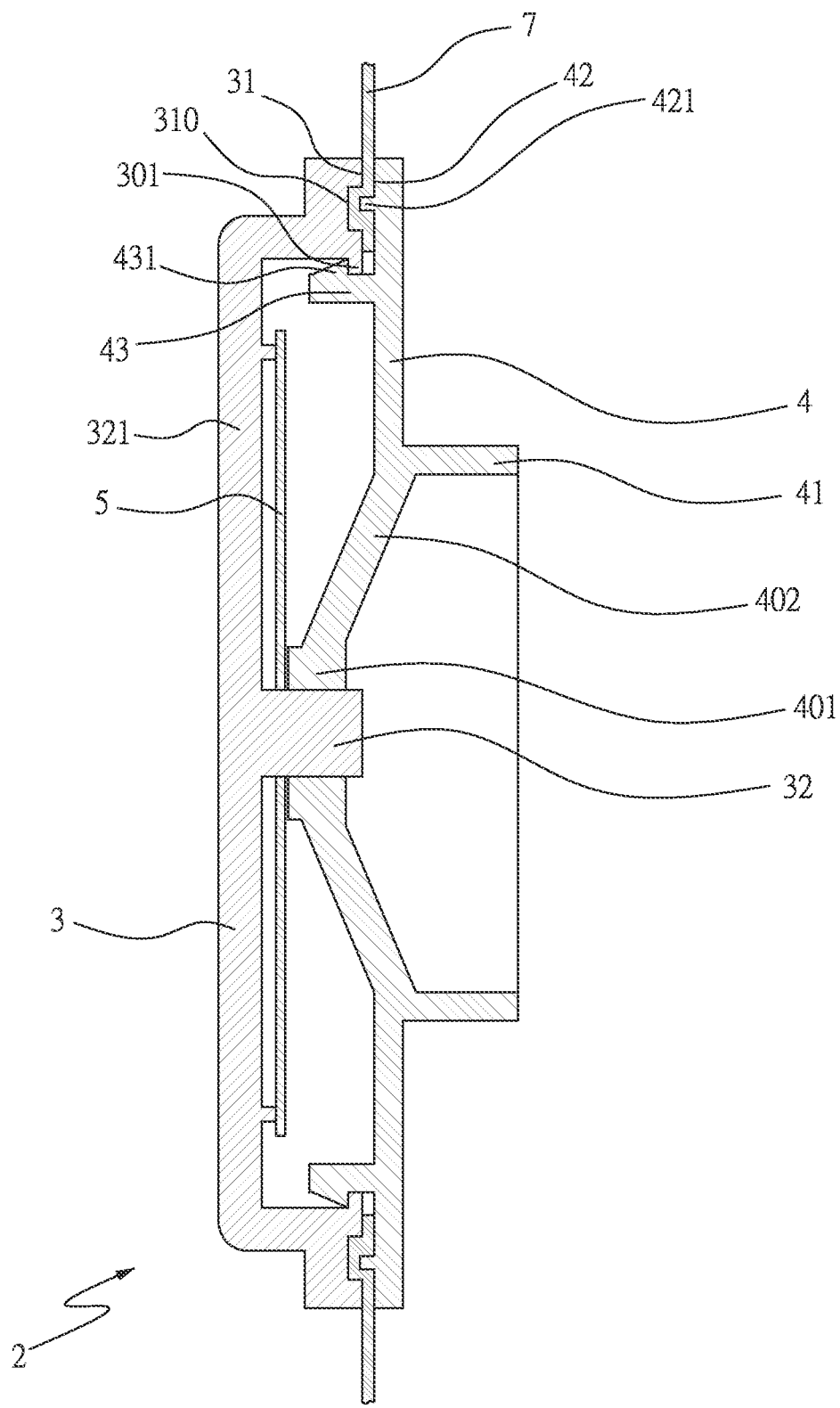
FIG. 5 shows a cross-section of the invention.

FIGS. 2 to 14 show an exterior illustration, exploded views, a cross-sectional view, and schematic views of a preferred embodiment and a further embodiment of the invention. Referring to FIGS. 2 to 14, it is clearly obtained that the invented valve 2 includes a base 3, an upper cover 4, a membrane 5 and a discharge device 6.

The base 3 has a chamber 30, a contact surface 31 and a pillar 32.

Multiple protrusions 301 are within the chamber 30, a groove 310 is on the contact surface 31, and the pillar 32 is situated in the middle of chamber 30 by the support of multiple first spokes 321, wherein gaps 322 are formed between the first spokes 321.

The upper cover 4 is set on the base 3 and has a space 40, an upper annular wall 41, a contact surface 42 and a lower annular wall 43, wherein there are multiple L-shaped engagement blocks 410 on the outer side of the upper annular wall 41.

An annular body 401 is situated in the space 40 through the support of multiple spokes 402, and is embedded into the pillar 32 of the base 3.

A bump 411 is in each of the L-shaped engagement blocks 410 on the outer side of the upper annular wall 41, a rib 421 is on the contact surface 42, and multiple projections 431 are on the lower annular wall 43.

The membrane 5 has a hole 50, and is embedded with pillar 32 of the base 3 through this hole 50.

The discharge device 6 has a combination hole 60. Multiple L-shaped engagement blocks 61 are on the combination hole 60. The L-shaped engagement blocks 61 are embedded into the L-shaped engagement blocks 410 of the upper annular wall 41 of the upper cover 4.

A bump 611 is on each of the L-shaped engagement blocks 61 of the combination hole 60.

The invented valve 2 is mainly assembled on respirator 7, the respirator 7 is interposed between the base 3 and the upper cover 4 (see FIG. 5), and the respirator 7 is pressed into and against the groove 310 of the contact surface 31 by rib 421 of the contact surface 42, so that the valve 2 can be firmly combined with respirator 7 and cannot slide or get loose. The base 3 and the upper cover 4 are in tight combination with each other through embedding the protrusions 301 of the base 3 into the projections 431 on the lower annular wall 43 of the upper cover 4, and embedding the annular body 401 of the upper cover 4 into the pillar 32 of the base 3.

In addition, when the annular body 401 of the upper cover 4 is embedded into the pillar 32 of the base 3, the annular body 401 restricts the position of the membrane 5 to prevent the arbitrary movement of the membrane 5.

Figure 6:
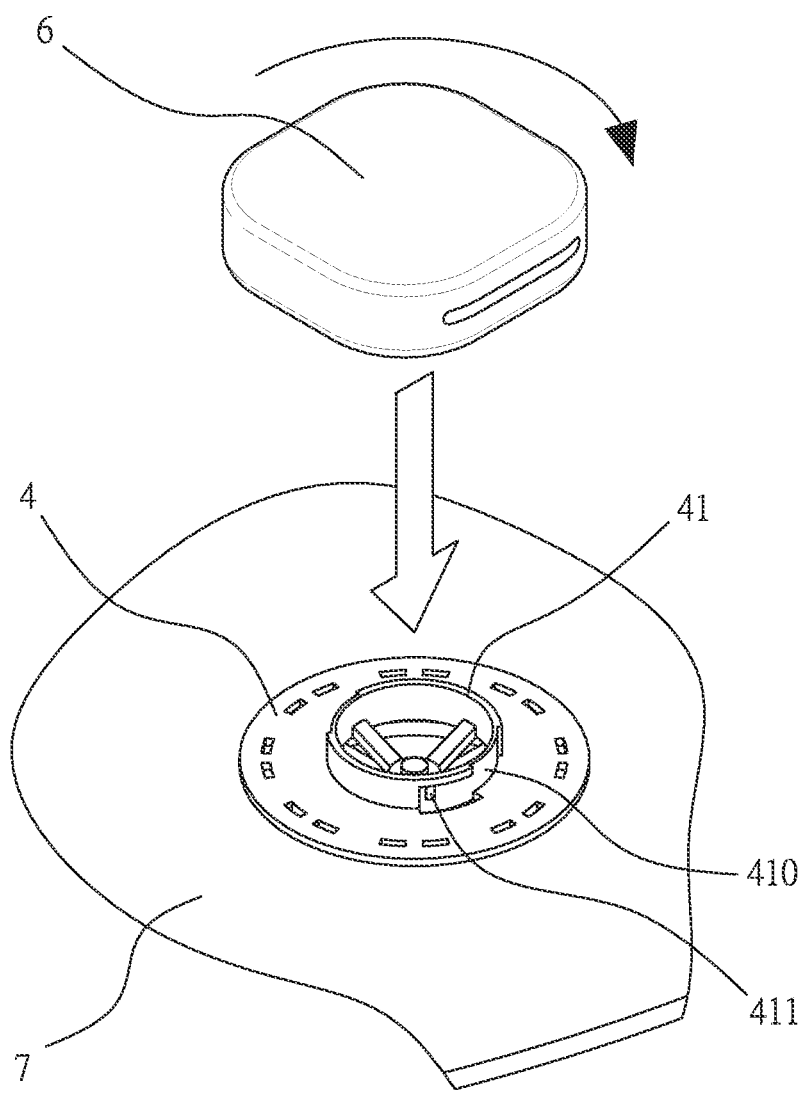
FIG. 6 shows a first schematic view of the preferred embodiment of the invention.
Figure 7:
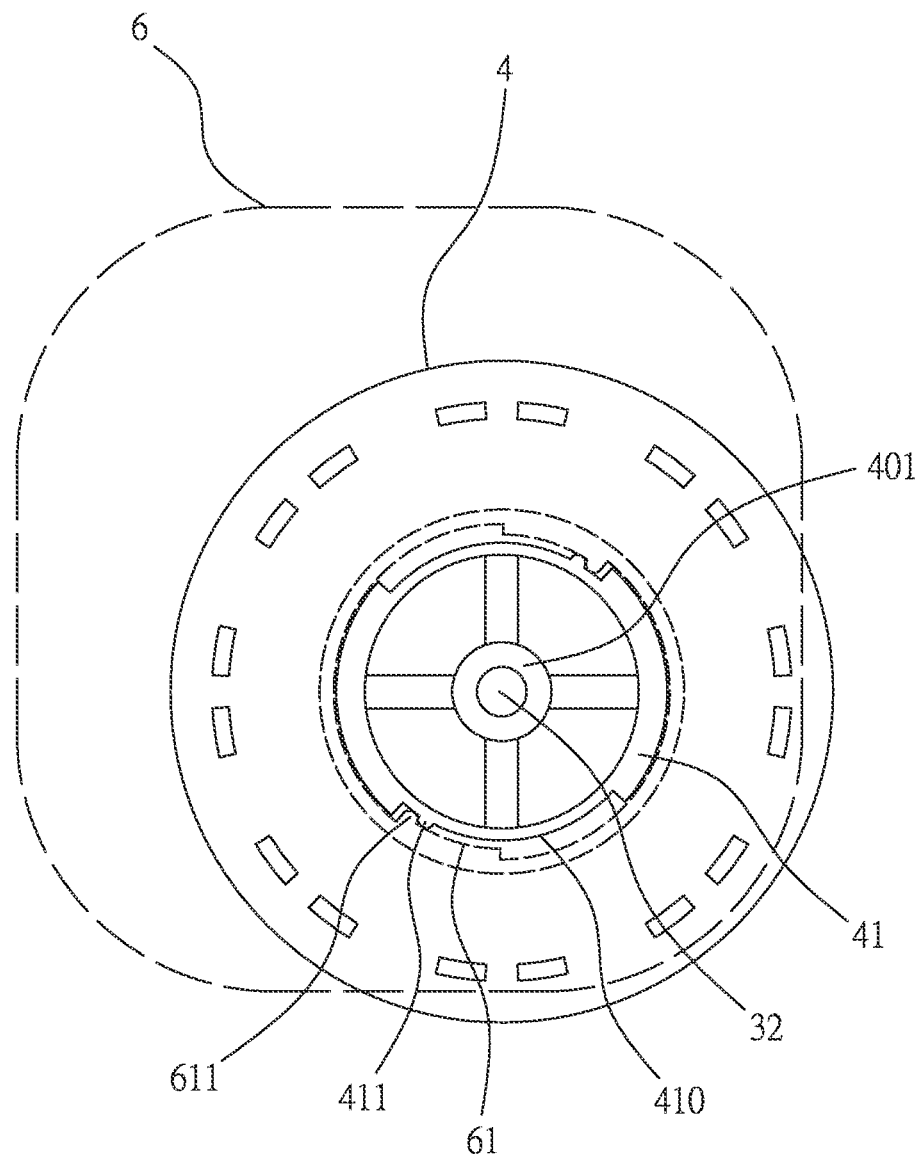
FIG. 7 shows a second schematic view of the preferred embodiment of the invention.

As mentioned hereinabove, when the discharge device 6 is to be assembled on the valve 2, the L-shaped engagement blocks 61 in the combination hole 60 are firstly vertically inserted into the L-shaped engagement blocks 410 of the upper annular wall 41, and then the discharge device 6 is rotated in a clockwise direction, so that the bumps 611 on the L-shaped engagement blocks 61 are pressed against the bumps 411 on the L-shaped engagement blocks 410, and the discharge device 6 can be firmly combined with the valve 2 (see FIGS. 6 and 7). When the discharge device 6 is to be detached, the discharge device 6 is rotated in a anticlockwise direction, so that the bumps 611 on the L-shaped engagement blocks 61 are separated from the bumps 411 on the L-shaped engagement blocks 410, and the discharge device 6 can be detached.

Figure 9:
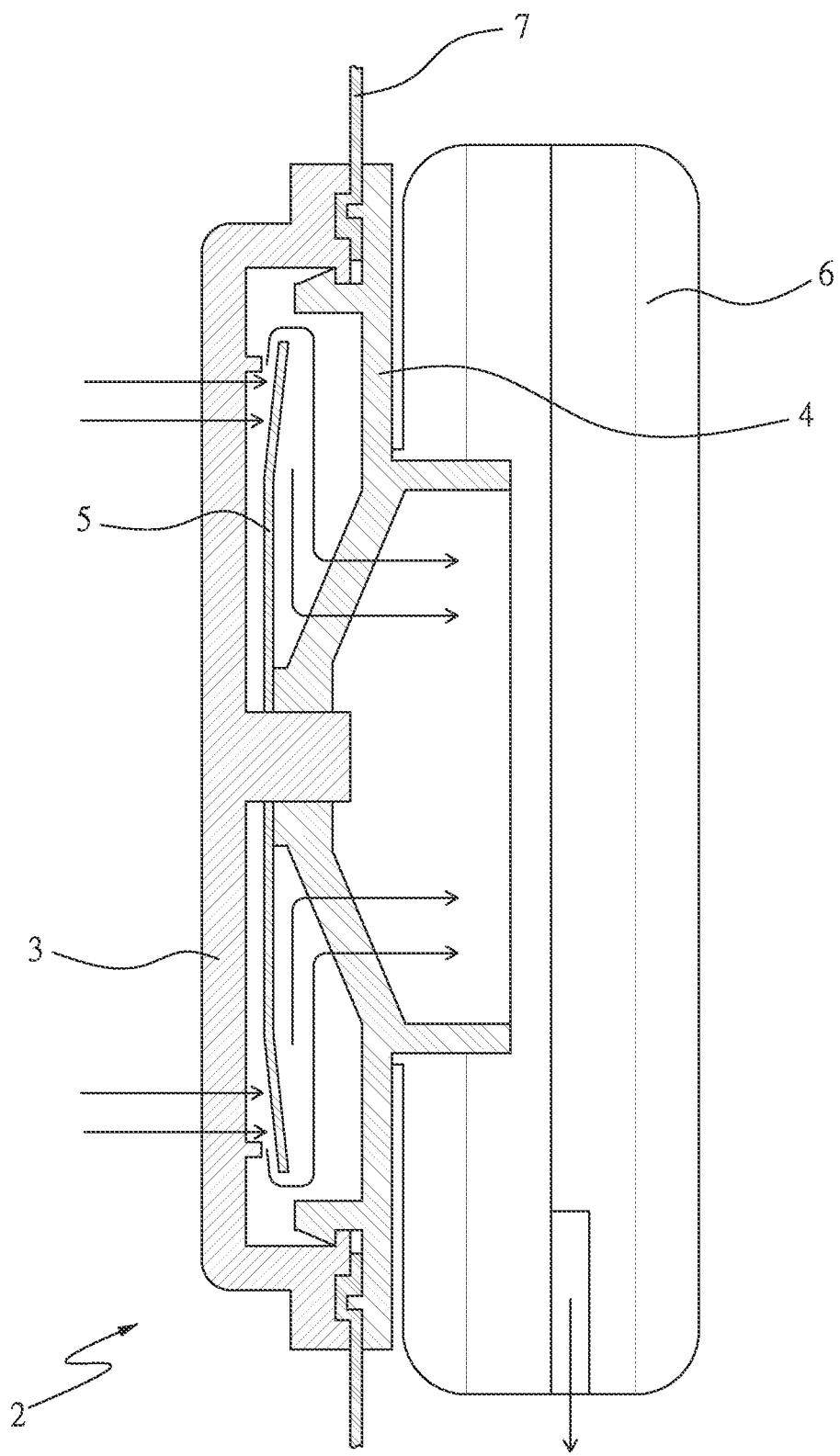
FIG. 9 shows a fourth schematic view of the preferred embodiment of the invention.

After the user has worn the respirator 7, the respirator 7 filters the external dirty, dust or germ when the user inhales; and when the user exhales, the pressure of the exhaled gas pushes away an edge of the membrane 5, the gas enters the chamber 30 of the base 3, and finally the discharge device 6 guides the gas out (see FIG. 9).

Figure 8:
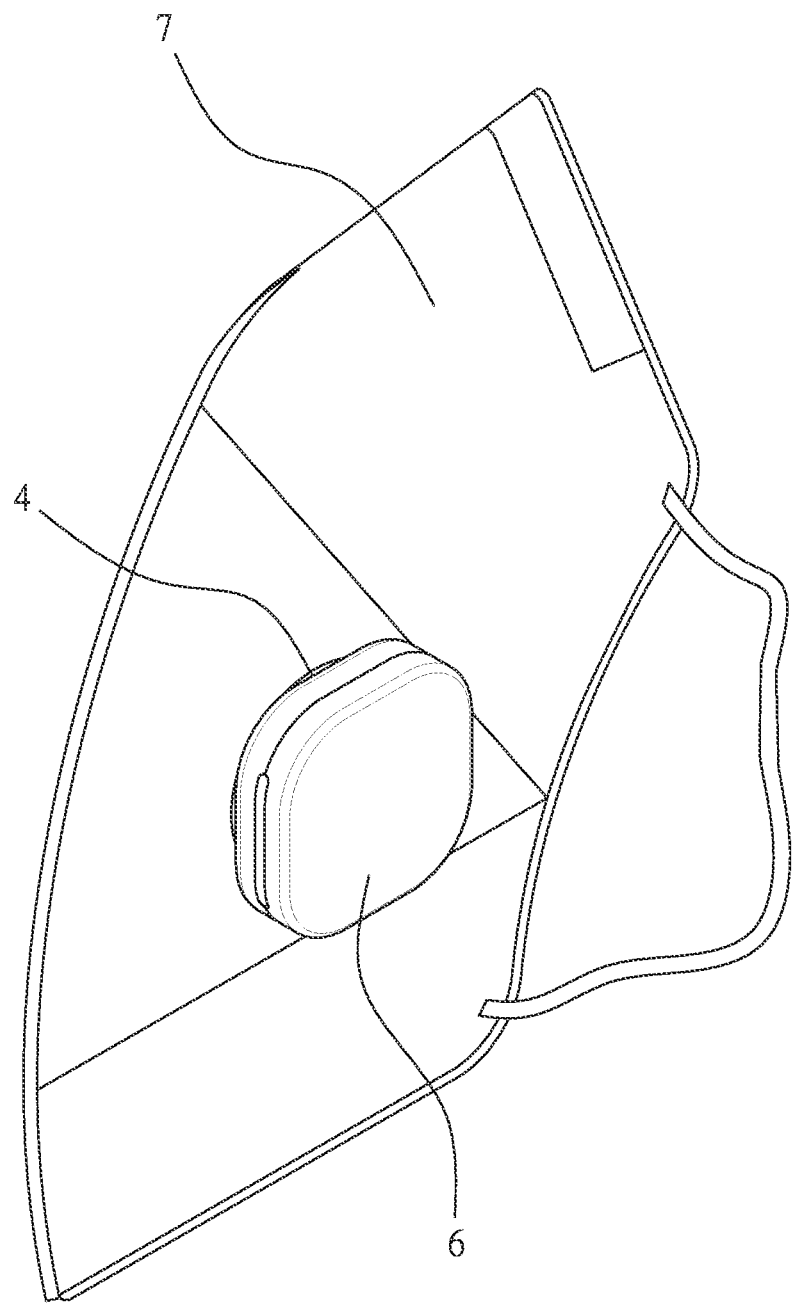
FIG. 8 shows a third schematic view of the preferred embodiment of the invention.
Figure 10:
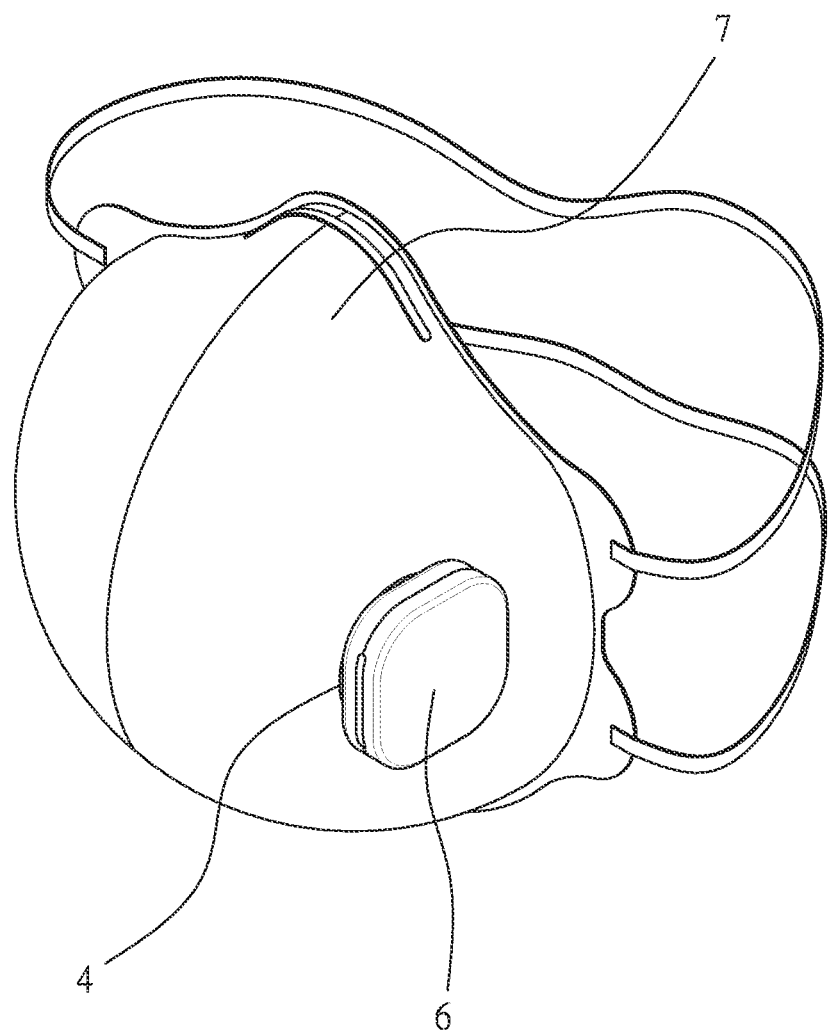
FIG. 10 shows a fifth schematic view of the preferred embodiment of the invention.

The invented valve 2 may be applied to not only the flat respirator 7 of FIG. 8, but also the cup-shaped respirator 7 of FIG. 10. Basically, the invented valve 2 can be applied to all commercially available associated respirators.

Figure 11:
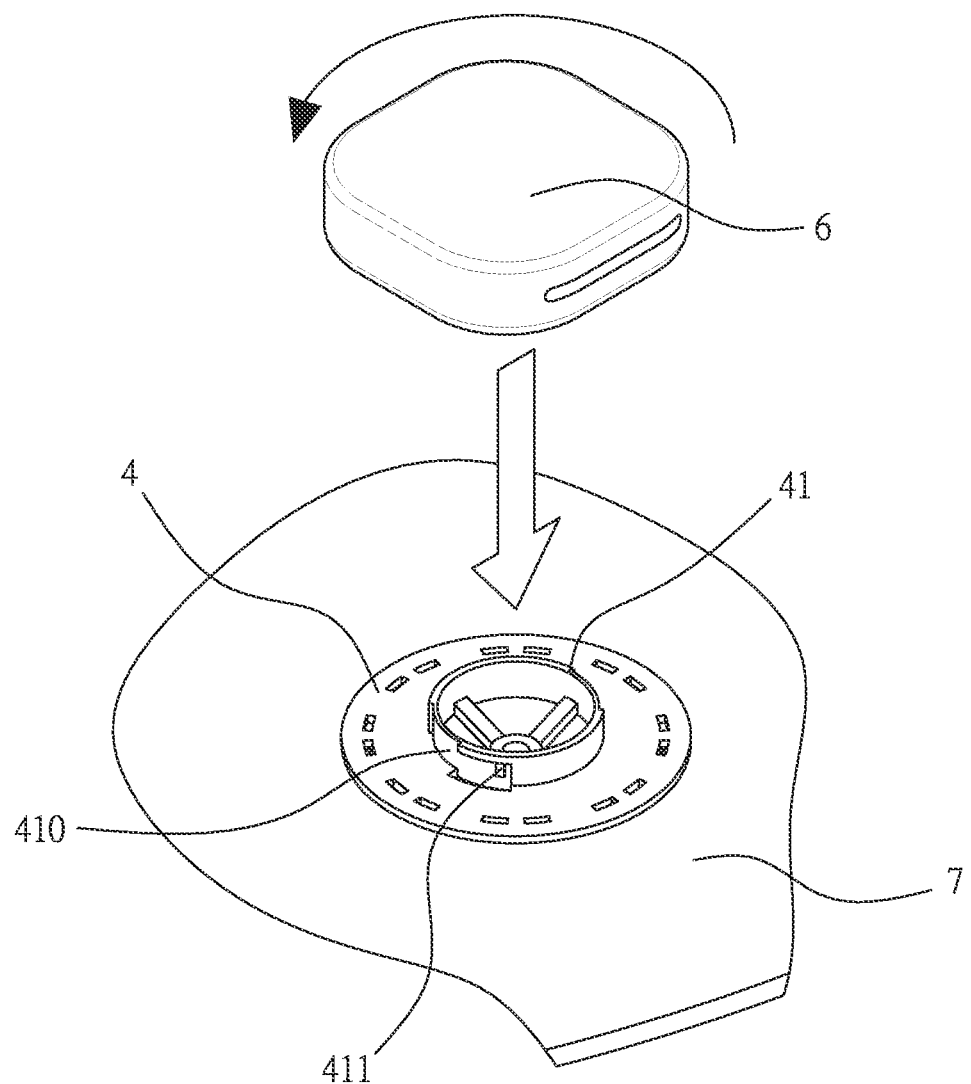
FIG. 11 shows a first schematic view of the further embodiment of the invention.
Figure 12:
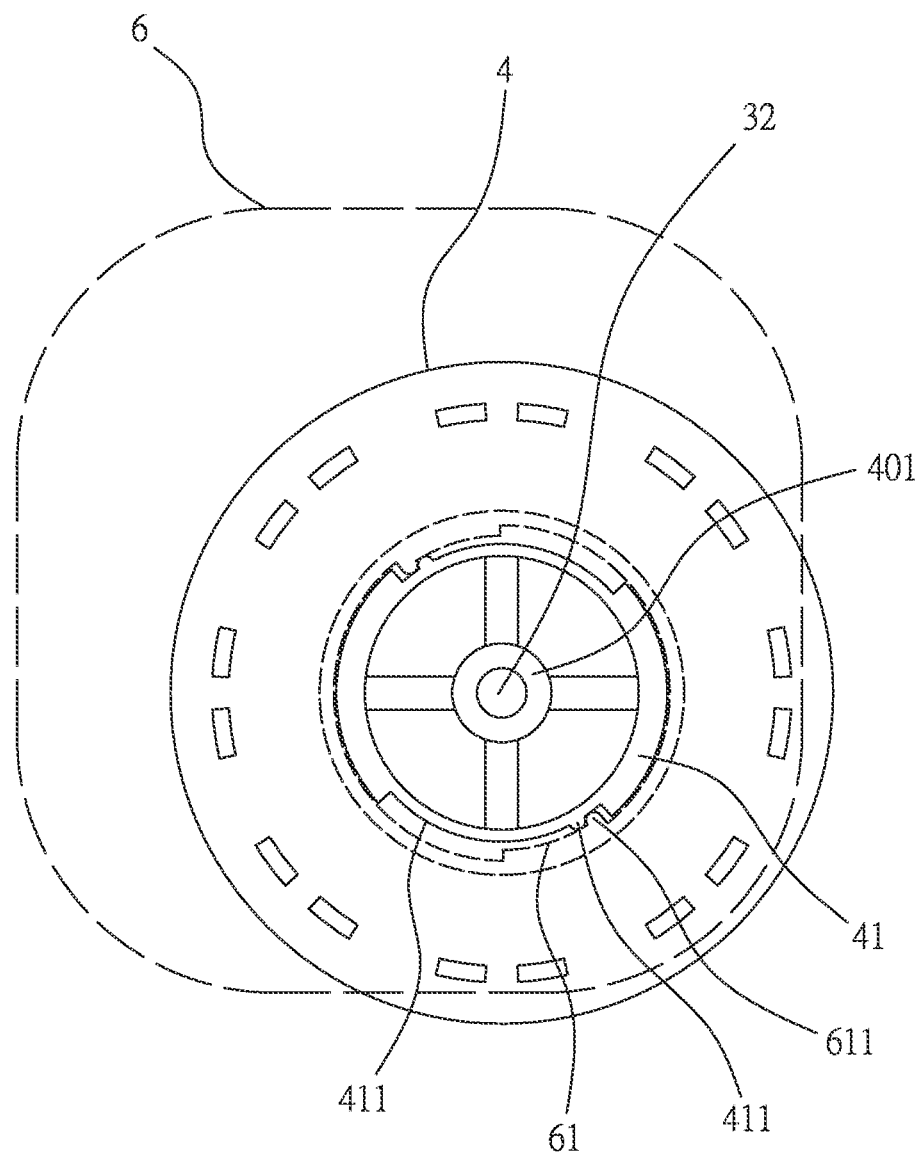
FIG. 12 shows a second schematic view of the further embodiment of the invention.

In addition, as shown in FIGS. 11 and 12, the L-shaped engagement blocks 410 of the upper annular wall 41 and the L-shaped engagement blocks 61 of the rotated discharge device 6 are in the pattern of the other direction. Similarly, the L-shaped engagement blocks 61 in the combination hole 60 are vertically inserted into the L-shaped engagement blocks 410 of the upper annular wall 41 first, and then the discharge device 6 is rotated anticlockwise, so that the bumps 611 on the L-shaped engagement blocks 61 press against the bumps 411 on the L-shaped engagement blocks 410, and the discharge device 6 can be firmly combined with the valve 2. When the discharge device 6 is to be detached, the discharge device 6 is rotated in the clockwise direction, so that the bumps 611 on the L-shaped engagement blocks 61 are separated from the bumps 411 of the L-shaped engagement blocks 410, and the discharge device 6 can be detached.

Figure 13:
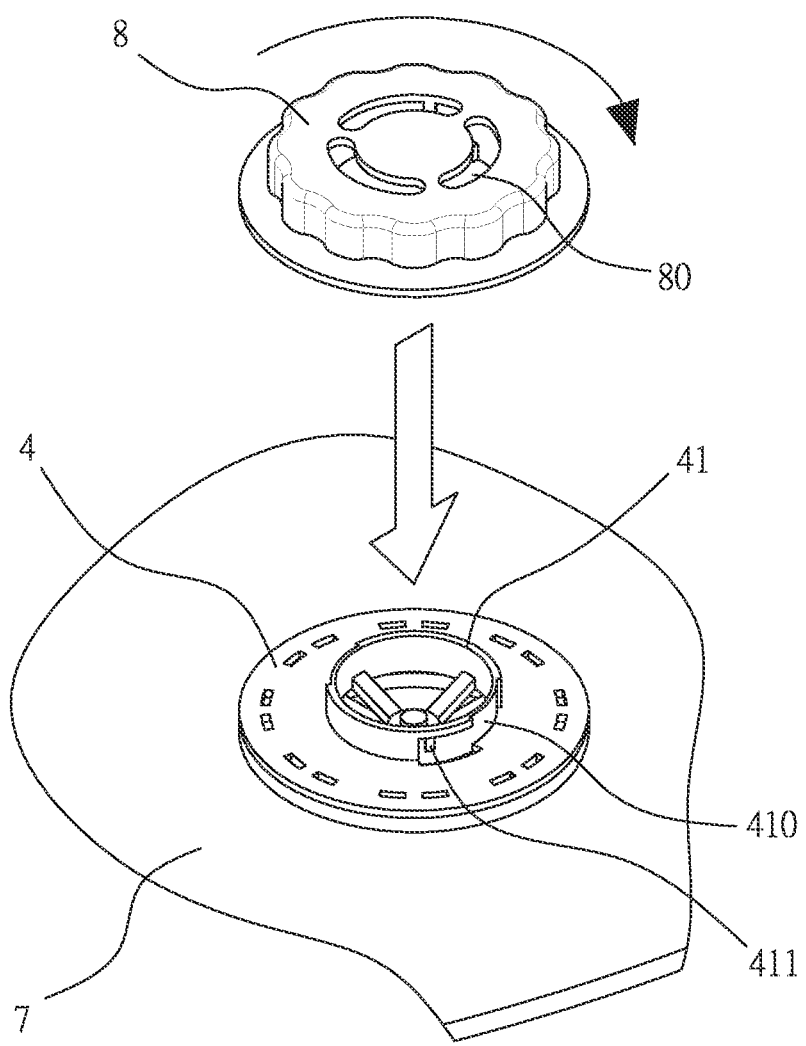
FIG. 13 shows a third schematic view of the further embodiment of the invention.
Figure 14:
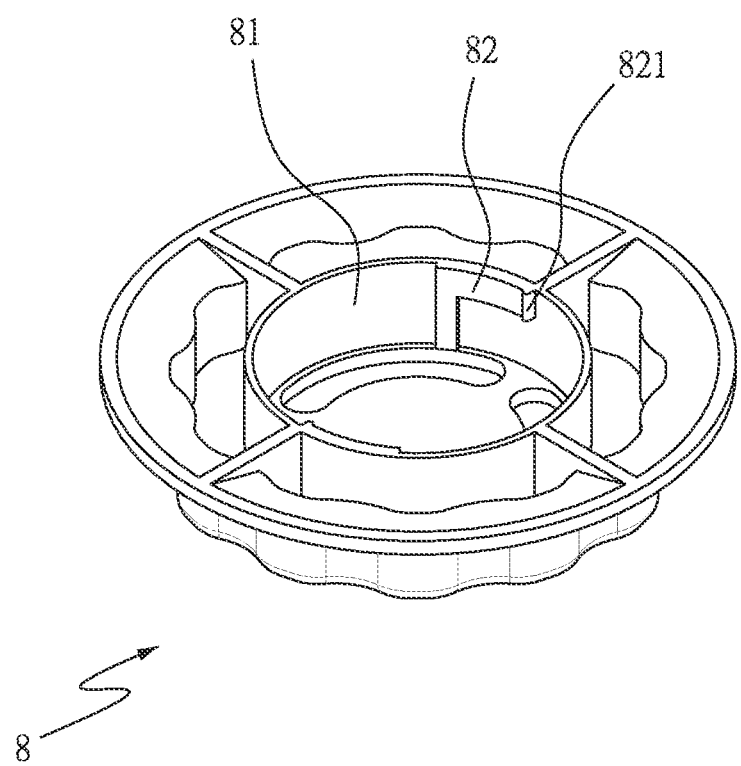
FIG. 14 shows a fourth schematic view of the further embodiment of the invention.

In addition to the mounting of the discharge device 6 onto the valve 2 of the invention, the discharge device 6 can be detached when the electric power of the discharge device 6 is exhausted. In order to prevent the external dirty or dust from entering the valve 2 after the discharge device 6 is detached, a shielding cover 8 may be additionally assembled, as shown in FIGS. 13 and 14. Multiple L-shaped engagement blocks 82 in the combination hole 81 at the bottom of the shielding cover 8 are vertically inserted into the L-shaped engagement blocks 410 of the upper annular wall 41, and then the shielding cover 8 is rotated in the clockwise direction, so that bumps 821 on the multiple L-shaped engagement blocks 82 press against the bumps 411 on the L-shaped engagement blocks 410. Thus, when the shielding cover 8 can be firmly combined with the valve 2 and after the user has worn the respirator 7, the pressure of the exhaled gas pushes away the edge of the membrane 5 when the user exhales, and the gas enters the chamber 30 of the base 3 and is then discharged from multiple holes 80 of the shielding cover 8.

The invented valve 2 may be combined with the above-mentioned discharge device 6 or shielding cover 8, and may also be combined with different types of accessories. Of course, the structures similar to the L-shaped engagement blocks 61 and the bumps 611 of the discharge device 6 must be provided to work in conjunction with the L-shaped engagement blocks 410 and the bumps 411 of the upper annular wall 41.

In summary, comparing with the drawback and inconvenience that the conventional respirator cannot be added with other assistant devices or components, the invented valve 2 has the following advantages. With the L-shaped engagement blocks 410 provided on the upper cover 4 and the multiple L-shaped engagement blocks 61 provided on the discharge device 6, the discharge device 6 can be attached and detached, or the shielding cover 8 can be replaced according to the requirements. Furthermore, other compatible accessories can be combined therewith, so that the convenience of using the respirator 7 is significantly increased. In addition, the discharge device 6 can be used to achieve the active discharge effect. Compared with the conventional passive discharge method, the invention can further enhance the wearer's comfort.

New characteristics and advantages of the invention covered by this document have been set forth in the foregoing description. It is to be expressly understood, however, that the drawings are for the purpose of illustration only and are not intended as a definition of the limits of the invention. Changes in methods, shapes, structures or devices may be made in details without exceeding the scope of the invention by those who are skilled in the art. The scope of the invention is, of course, defined in the language in which the appended claims are expressed.

What is claimed is:

1. A valve structure for a respirator, the valve structure comprising:
    a base having a chamber, a first contact surface and a pillar, wherein a plurality of protrusions are provided in the chamber, and a groove is provided on the first contact surface;
    an upper cover, which is disposed on the base and has a space, an upper annular wall, a second contact surface and a lower annular wall, wherein an outer side of the upper annular wall is provided with a plurality of first L-shaped engagement blocks, a rib is provided on the second contact surface of the upper cover and extends into the groove of the first contact surface, and a plurality of projections are provided on the lower annular wall of the upper cover;
    a membrane, which has a hole and is disposed on the pillar of the base through the hole; and
    a discharge device having a combination hole, on which a plurality of second L-shaped engagement blocks are provided, wherein the first L-shaped engagement blocks are embedded into the second L-shaped engagement blocks on the upper annular wall;
    wherein a respirator is pressed into and against the groove of the first contact surface by the rib of the second contact surface;
    wherein the base and the upper cover are in tight combination with each other through embedding the protrusions of the base into the projections on the lower annular wall of the upper cover.

2. The valve structure according to claim 1, wherein the pillar of the base is placed in the chamber through a plurality of first spokes.

3. The valve structure according to claim 1, wherein an annular body is provided in the space of the upper cover through a plurality of second spokes, and the annular body is embedded into the pillar of the base.

4. The valve structure according to claim 1, wherein a bump is provided in each of the first L-shaped engagement blocks provided on the outer side of the upper annular wall.

5. The valve structure according to claim 1, wherein each of the second L-shaped engagement blocks of the combination hole is provided with a bump.

* * * * *